United States Patent
Siebert et al.

(10) Patent No.: US 12,171,604 B2
(45) Date of Patent: Dec. 24, 2024

(54) COMPUTER-IMPLEMENTED METHOD FOR EVALUATING AN X-RAY IMAGE SHOWING A CONTRAST AGENT, EVALUATION FACILITY, X-RAY FACILITY, COMPUTER PROGRAM AND ELECTRONICALLY READABLE DATA CARRIER

(71) Applicant: Siemens Healthcare GmbH, Erlangen (DE)

(72) Inventors: Anke Siebert, Nuremberg (DE); Philipp Bernhardt, Forchheim (DE); Bernhard Christian Meyer, Hannover (DE); Thomas Werncke, Wandlitz (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/215,666

(22) Filed: Jun. 28, 2023

(65) Prior Publication Data

US 2024/0008831 A1   Jan. 11, 2024

(30) Foreign Application Priority Data

Jul. 11, 2022   (DE) ..................... 10 2022 207 026.7

(51) Int. Cl.
*A61B 6/00* (2006.01)
*G06T 7/136* (2017.01)
*A61B 6/50* (2024.01)

(52) U.S. Cl.
CPC ............ *A61B 6/481* (2013.01); *A61B 6/4441* (2013.01); *G06T 7/136* (2017.01); *A61B 6/504* (2013.01);
(Continued)

(58) Field of Classification Search
CPC ...................................................... A61B 6/414
See application file for complete search history.

(56) References Cited

U.S. PATENT DOCUMENTS

| | | | |
|---|---|---|---|
| 2017/0287132 A1 | 10/2017 | Ertel et al. | |
| 2021/0137479 A1* | 5/2021 | König | A61B 6/4441 |
| 2021/0192739 A1 | 6/2021 | Tashenov | |

FOREIGN PATENT DOCUMENTS

| | | |
|---|---|---|
| CN | 108514425 A | 9/2018 |
| DE | 102016205507 A1 | 10/2017 |
| DE | 102019220147 A1 | 6/2021 |

OTHER PUBLICATIONS

Hubbell, J. H., and Seltzer, S. M., "Tables of x-ray mass attenuation coefficients and mass energy-absorption coefficients 1 keV to 20 meV for elements z = 1 to 92 and 48 additional substances of dosimetric interest," Radiation Physics Division, PML NIST, pp. 1-5 (1995).

(Continued)

*Primary Examiner* — Dani Fox
(74) *Attorney, Agent, or Firm* — Lempia Summerfield Katz LLC

(57) ABSTRACT

A computer-implemented method for evaluating an X-ray image includes: segmenting the hollow organ structure in the X-ray image; determining center lines and edge boundaries of the segmented hollow organ structure and ascertaining a diameter of each hollow organ along its center line; ascertaining an image absorption value, describing the increase in absorption due to a contrast agent in the hollow organ compared to surroundings of the hollow organ, along the center line of each hollow organ; ascertaining, for each image absorption value, a theoretical computing absorption value expected when the hollow organ is completely filled with the contrast agent, by using at least the diameter and contrast agent information; determining a filling level along (Continued)

the center line of each hollow organ of the hollow organ structure by comparing the image absorption value with the computing absorption value; and outputting filling level information including the filling levels.

13 Claims, 3 Drawing Sheets

(52) U.S. Cl.
CPC .............. *G06T 2207/10116* (2013.01); *G06T 2207/30101* (2013.01)

(56) References Cited

OTHER PUBLICATIONS

Wikipedia "Lambert-Beer's law" Retrieved Nov. 24, 2021. https://web.archive.org/web/20210924143012/https://de.wikipedia.org/wiki/Lambert-beersches_Gesetz, pp. 1-9.

\* cited by examiner

COMPUTER-IMPLEMENTED METHOD FOR EVALUATING AN X-RAY IMAGE SHOWING A CONTRAST AGENT, EVALUATION FACILITY, X-RAY FACILITY, COMPUTER PROGRAM AND ELECTRONICALLY READABLE DATA CARRIER

The present patent document claims the benefit of German Patent Application No. 10 2022 207 026.7, filed Jul. 11, 2022, which is hereby incorporated by reference in its entirety.

TECHNICAL FIELD

The disclosure relates to a computer-implemented method for evaluating a two-dimensional X-ray image showing a contrast agent in a hollow organ structure, (e.g., a vascular tree), in a recording region of a patient, recorded with an X-ray facility using X-ray radiation of an X-ray spectrum. In addition, the disclosure relates to an evaluation facility, an X-ray facility, a computer program, and an electronically readable data carrier.

BACKGROUND

The use of contrast agents in X-ray imaging is known. A particularly well-established component of contrast agents is iodine. Iodine absorbs X-ray radiation to a much greater degree than other conventional materials that occur inside a person, so there is a strong contrast of the hollow organ structures, (e.g., blood vessels), filled with the iodine. Other contrast agents are also used, in particular for the case of iodine incompatibilities, for example, carbon dioxide or carbon dioxide-containing contrast agents. Different fields of application may exist in this connection, (such as digital subtraction angiography (DSA)), in which contrast agent is introduced as what is known as a contrast agent bolus into vascular branches of a patient for examination, it being possible to record X-ray images with and X-ray images without contrast agent in DSA and to subtract these images from each other, so only the vessels filled with contrast agent remain. Contrast agent is also used in other ways, however, in order to highlight particular hollow organ structures, particular blood vessels in vascular branches, for example, in the fluoroscopic monitoring of, in particular, minimally invasive procedures or in the case of other radiographic and/or fluoroscopic examination of dynamics, for example, the blood circulation of particular regions of tissue. In the example of the vascular tree, the administered contrast agent moves with the blood through the blood vessels. This flow of the contrast agent is conventionally measured by a series of X-ray images using a particular frame rate. These are conventionally two-dimensional X-ray images, with three-dimensional contrast agent-imaging approaches also having been proposed already, but these are, of course, likewise based on the recording of two-dimensional X-ray images, for example projection images from different directions of projection.

For the best possible visibility of the contrast agent and thus of the hollow organs of the hollow organ structure, it is helpful to attain a high filling level of the hollow organ with the contrast agent because the greatest contrasts are obtained in the X-ray image in this way. The amount of contrast agent, and thus the fill level, may be controlled by the filling pressure during the administration of the contrast agent, and this may occur manually or using an automatic contrast agent-administering facility, for example, a contrast agent injector. If the filling pressure is too high, however, there is also a risk of damage to the hollow organ, for example, a rupture of a blood vessel because the hollow organ may only hold what it normally also transports, for example, only the blood, which is transported during normal blood flow.

With manual administering of contrast agents, the filling pressure may be controlled, for example, owing to the resulting mechanical feedback, it being possible for the contrast of the hollow organ in an X-ray image already recorded during administering to serve as a further possibility. While the first-mentioned procedure requires a lot of experience, the appearance of an X-ray image also depends to a great extent on other parameters, which have to be taken into consideration.

SUMMARY AND DESCRIPTION

The disclosure is therefore based on the object of providing improved, in particular real-time capable, feedback following an administration of contrast agent.

The scope of the present disclosure is defined solely by the appended claims and is not affected to any degree by the statements within this summary. The present embodiments may obviate one or more of the drawbacks or limitations in the related art.

In order to achieve this object, a computer-implemented method, an evaluation facility, an X-ray facility, a computer program, and an electronically readable data carrier are disclosed herein.

A method of the type described herein includes segmenting the hollow organ structure in the X-ray image. The method further includes determining center lines and edge boundaries of the segmented hollow organ structure and ascertaining a respective diameter of each hollow organ in the segmented hollow organ structure along its center line. The method further includes ascertaining an image absorption value, describing the increase in absorption due to the contrast agent in the hollow organ compared to a surroundings of the hollow organ in the X-ray image, along the center line of each hollow organ, in particular for each position along the center line for which a diameter was ascertained. The method further includes ascertaining for each image absorption value a theoretical computing absorption value expected when the hollow organ is completely filled with the contrast agent, by using at least the diameter and contrast agent information describing a composition and/or the absorption properties of the contrast agent. The method further includes determining a filling level along the center line of each hollow organ of the hollow organ structure by comparing the image absorption value with the computing absorption value. The method further includes outputting filling level information including the filling levels.

The disclosure therefore proposes an automatic assessment of filling levels with contrast agent in the hollow organs of the hollow organ structure, (e.g., blood vessels of the vascular tree), at the instant of recording of the X-ray image, which is easy to implement, (e.g., in real time), and supplies feedback, (e.g., to a user). A user, who has administered the contrast agent themselves before recording the X-ray image, thus advantageously obtains outstanding feedback about how well the hollow organs of the hollow organ structure are filled and how great their capabilities already are in administering contrast agent. In particular, the user may assess how close they are to the optimum use of contrast agents. In this way, the user no longer has to estimate for themselves, and this is becoming increasingly more difficult on the basis of displayed X-ray images because a large number of recording techniques and also image post-processing acts are used. In particular, image processing nowadays is less about the representation of actual absorption maps and more about an interpretation of the X-ray images in such a way that all relevant structures are already highly visible in the first recording without and with post-processing acts.

In other words, it is also conceivable within the framework of the present disclosure to forward the filling level information in addition to or as an alternative to other evaluation units and/or control units in order to derive further information, (e.g., statistical information) from them, to improve control programs for automatic contrast agent-administering facilities, and/or to adapt the actuation of automatic contrast agent-administering facilities so as to actually be up-to-date, as will be set forth in more detail.

Overall, the present disclosure promotes the more optimum use of contrast agents and also reduces the risk of damage to the hollow organs in the process.

In this connection, the disclosure utilizes the fact that with regard to segmenting hollow organ structures, in particular vascular branches, a large number of possibilities exists in the meantime, exactly as for determining center lines, diameters, and the like, which may be implemented partially in real time and may also be used advantageously within the framework of the present disclosure. Known segmenting approaches, which may also be used within the framework of the present disclosure, may include threshold value-based approaches, "region-growing" approaches, the use of classifiers, and/or methods supported by anatomical atlases. In particular, at least partially trained functions of artificial intelligence, (e.g., neural networks such as Convolutional Neural Networks (CNN)), may also be used for the acts of segmenting and determining the center lines and edge boundaries and the diameters. These permit especially fast image evaluation and analysis.

Segmenting and optionally determining center lines, edge boundaries, and diameters may also include additional information apart from the X-ray image. For example, it is basically conceivable to work not solely on individual two-dimensional X-ray images but to also use other X-ray images of a series of X-ray images by way of support. In embodiments of this kind, it is also possible, when X-ray images from different directions of projection are present, to work on reconstructed, three-dimensional image datasets, (e.g., also perform three-dimensional segmenting therefore), the effects of which on the two-dimensional X-ray images may be easily derived owing to the known projection geometries. This means edge boundaries, center lines, and/or diameters may be back-calculated from the three-dimensional space into the two-dimensional space of the X-ray images again. In particular, with regard to potential superimpositions of hollow organs, (e.g., blood vessels), approaches are also conceivable, moreover, in which, for example, with a biplane X-ray facility, X-ray images may simultaneously be recorded from different recording geometries, (e.g., at a 90° angle to each other). From this, it is possible to derive vascular courses more easily in the vascular tree. It is also conceivable and robustly practicable with modern methods, to perform segmenting directly in the two-dimensional X-ray image. Additional information may also be taken into consideration here, for example, segmenting results for X-ray images recorded previously, other prior recordings of the patient, and/or anatomical atlases.

Within the framework of the present disclosure, it may be expedient overall to assume that the hollow organs are round. In particular, the diameter in the segmented hollow organ structure and/or the computing absorption value is ascertained under the assumption of a circular cross-section of the respective hollow organ. This not only makes a simple calculation possible, but also only one characteristic value, the one diameter, at each corresponding position along the center lines has to be provided.

Apart from determining the center line and the diameter, the segmenting result is also used to measure the absorption actually visible in the X-ray image due to the contrast agent. An image absorption value is determined for this purpose, which ultimately states by how much greater the X-ray absorption turns out to be in the hollow organ due to the contrast agent than next to it, (e.g., directly next to it), in the surroundings therefore. One embodiment provides that, for ascertaining the image absorption value, the ratio of the amount of the difference of a hollow organ image value in a center line region including at least one image point around the center line and an image value of the surroundings in a reference region including at least one image point and located outside of the segmented hollow organ structure from the image value of the surroundings of the reference region is ascertained. For this act, it is again beneficial that the segmenting result exists, in particular also the information on the edge boundary, because this also contains the information about whether an image point is situated inside or outside of the hollow organ structure. The image value of the surroundings, which states how much absorption there is in the patient without contrast agent, is therefore considered to be a reference, because the absorption is also given for the hollow organ and thus X-ray beams passing through contrast agent. Accordingly, it is proposed, in order to measure the share of additional absorption due to the contrast agent in the hollow organ structure, that the difference is formed between the image value in the center of the hollow organ, the hollow organ image value therefore, and the image value outside of the hollow organ, the image value of the surroundings therefore, which describes the additional absorption. This difference is set in a ratio to the image value of the surroundings, so the image absorption value ultimately describes which proportion of the surroundings absorption additionally takes place in the hollow organ due to the contrast agent.

The image absorption value accordingly includes image values, (e.g., grayscale values), from outside and inside the hollow organ structure. In other words, the image absorption value is ascertained as a function of at least one image value respectively, inside and outside of the segmented hollow organ structure. Expediently, those positions along the center lines for which a diameter is also known are selected here to be able to easily ascertain the computing absorption value there. The image value inside the corresponding hollow organ may then be taken on the center line at this position, while outside of the hollow organ structure it is possible to measure at different locations, but at least one image value in the immediate surroundings of the hollow organ may be selected at this position of its center line.

It is basically conceivable in this connection to use as the center line region only the image point including the center line at the corresponding position, so the corresponding image value, in particular grayscale value, exists directly. Accordingly, an individual image point also outside of the hollow organ, in particular as close as possible to this position, and thus the image point forming the center line region, may be used as a reference region. It may also be expedient, e.g., if a statistical summary is to be carried out, to use center line regions and/or reference regions including a plurality of image points. It may then be provided that in the case of a center line region including a plurality of image points, the hollow organ image value and/or in the case of a reference region including a plurality of image points, the image value of the surroundings is ascertained by statistical, in particular weighted, averaging of the image values of the X-ray image over these image points. The expediency of using a plurality of image points may also depend, in particular, on the spatial resolution of the X-ray image. If a plurality of image points is to be used, nine image points or sixteen image points, for example, may be used. An outlier detection is optionally also conceivable in this connection.

The reference region may particularly advantageously lie immediately adjoining the hollow organ and/or in a cutting plane running through the center line region, e.g., perpendicular to the center line. With a two-dimensional X-ray image, straight lines standing perpendicular on the center line (as part of such cutting planes), for example, may be defined, with progress being made along these straight lines, starting from the center line, (e.g., by at least half the diameter), until the surroundings of the hollow organ and the hollow organ structure is reached in accordance with the segmenting result. For example, at least the first and/or the second image point located outside of the hollow organ structure may then be used as part of the reference region, and this may be performed, in particular, also on both sides.

Owing to the construction performed in this specific exemplary embodiment for ascertaining the image absorption value, the image absorption value corresponds at least substantially to the result of an application of the Beer Lambert law to the amount of contrast agent actually radiographed. In other words, the image value of the surroundings describes the basic radiation intensity, which is attenuated further by the contrast agent, and, more precisely, by the described difference between image value of the surroundings and hollow organ image value. The quotient thus at least substantially reproduces that which is expressed by the Beer Lambert law, which forms the quotient from attenuated intensity and incident intensity as an exponential function dependent on the amount of material radiographed.

Accordingly, an expedient development also provides that for ascertaining the computing absorption value, the Beer Lambert law is used for X-ray radiation of the X-ray spectrum, which passes through a section of the contrast agent of the contrast agent composition corresponding to the diameter. It is assumed therefore that the hollow organ, in particular the blood vessel, is completely filled with contrast agent and the theoretical absorption calculated for this filling level of 100%, with the contrast agent used and the diameter of the hollow organ, in particular assuming a perfectly cylindrical shape, being used. A simple calculation rule is given thereby, which enables extremely fast ascertainment of the computing absorption value.

If the image absorption value is determined, as specifically proposed, as a quotient of the difference and the image value of the surroundings and the computing absorption value by the Beer Lambert law, it is possible to directly compare the two absorption values. In particular, a filling level then results, for example by way of division of the image absorption value by the computing absorption value, by way of division of the measured absorption by the expected absorption therefore.

The X-ray spectrum, which may be described by spectrum information, may also be taken into consideration by way of the description of the extinction in the contrast agent by an extinction value. It may be provided in this connection that filtering that has already taken place in the beam path is also considered in the spectrum information. While it is basically possible within the framework of the Beer Lambert law to provide extinction values for different items of spectrum information, for example, including a voltage of the X-ray tube with which the X-ray spectrum was generated, as a functional correlation and/or Look-Up table, a simplification is also conceivable within the framework of the present disclosure, in particular when the extinction value changes only slightly or slowly with the spectrum information. It may then be provided, for example, that in order to take into consideration the X-ray spectrum, extinction values for high-energy and low-energy X-ray spectra respectively are provided. For example, it may be provided that a limit value is defined for the tube voltage, above which high-energy X-ray spectra are generated, but below which low-energy X-ray spectra are generated. Embodiments of this kind are expedient, in particular, with regard to dual-energy imaging when two pre-defined spectra, for example, a high-energy spectrum and a low-energy spectrum, are used.

Furthermore, it may also be provided in this connection that the spectrum information is modified in order to take into consideration a beam hardening of X-ray radiation due to the patient, in particular as a function of a relative position of the respective hollow organ in the patient. This takes account of the correlation that with increasing radiography of the patient, the spectrum is shifted to higher energy levels, and this may be described as a beam hardening effect. This may also be taken into consideration if the relative position of the hollow organ in the patient may be estimated, and it is thus possible to also take into consideration to what extent the beam hardening has already changed the X-ray spectrum. A further increase in the accuracy of the filling level information is thus possible. This consideration of the beam hardening represents an expedient consideration of further imaging effects when assessing the filling level. This may also be advantageous.

It may therefore be provided that when ascertaining the computing absorption value and/or the image absorption value, at least one further imaging effect, (e.g., a beam hardening and/or a scattered radiation effect), are taken into consideration. While it is basically conceivable to apply known correction measures to the X-ray image, this may not be carried out in the case of two-dimensional X-ray images in which the absolute value with regard to the attenuation is frequently of no interest. In this connection, the present disclosure may then provide that, at least for ascertaining the filling level, these corrections, (e.g., a beam hardening correction and/or a scattered radiation correction), are nevertheless applied to the X-ray image. However, the at least one corresponding correction may also be introduced when ascertaining the computing absorption value. A corresponding approach with regard to the spectrum information has already been described for the beam hardening.

For scattered radiation correction, it is possible in a specific exemplary embodiment to provide particularly advantageously that a percentage correction value, describing, in particular, the ratio of scattered radiation to overall signal for the reference region, is ascertained and the share of the computing absorption value, ascertained, in particular using the Beer Lambert law, corresponding to the correction value is subtracted from it. This case therefore exploits the fact that a known variable, which describes the percentage share of the scattered radiation in the overall signal at the detector and is frequently referred to as "S/T", may be easily used for scattered radiation correction. This is because, when ascertaining the image absorption value, scattered radiation shares, for which a constant offset may be assumed, may become noticeable in the difference, but not in the image value of the surroundings. Therefore, when forming the ratio with the computing absorption value (not taking any scattered radiation into consideration), a deviation may occur. However, it may be seen that this deviation ceases to exist exactly when the computing absorption value is reduced by a share of itself, which matches the ratio of scattered radiation signal to the overall signal (scattered radiation signal plus image value of the surroundings). It is also conceivable to apply such a correction in another way, for example, multiplicatively with regard to the image absorption value.

In particular, when the contrast agent was administered manually, the filling level information may particularly advantageously be displayed at least partially on a display facility, in particular a display facility of the X-ray facility. The user acquires knowledge of the filling level in this way and for future administrations of contrast agent may learn from this, receives direct feedback therefore, how good their use of the contrast agent is.

For example, it may be provided that the filling level is displayed superimposed and spatially resolved, (e.g., color-coded), in the X-ray image and/or a hollow organ structure map derived from the segmented hollow organ structure. Hollow organ structure maps of this kind, which may be derived from segmenting results, are basically already known, (e.g., as a vascular tree map or "vessel map"). It may therefore be provided, in particular, that the filling levels are superimposed, in particular color-coded, on such a hollow organ structure map or the X-ray image itself. In certain examples, such as in the case of color-coded displays, warning colors, (e.g., red tones), may be used with filling levels above a threshold value, e.g., 95-100%. In this way, the view of the user may be immediately directed to regions in which an outstanding or optionally also excessive contrast agent filling exists. This applies, in particular, if the warning colors are used for filling levels above 100% (if, for example, the hollow organ, in particular blood vessel, is stretched even).

Alternatively, or additionally, it may also be provided that a maximum value of the filling level is represented as a number. This number may take place together with a display of the X-ray image and/or a hollow organ structure map, in particular at the edge or in a corner of the image or the map and/or in an associated display region. The maximum filling level may be a particularly relevant item of information, which may be particularly advantageously additionally provided.

As already mentioned, the filling level information may also be used otherwise, however, for example may be forwarded to an evaluation unit for evaluation, be displayed for subsequent consideration, be used for documentation and the like. This is particularly expedient when an automatic contrast agent-administering facility is used, (e.g., an automatic contrast agent injector is used). Based on such filling level information, for example, actuation of the administering facility may then be optimized on the basis of the filling level information.

It is also conceivable to take the filling level information into consideration directly in a control and/or regulation system. It may thus be provided that the filling level information is output as feedback information to a control unit of an automatic contrast agent-administering facility administering the contrast agent, where it is taken into consideration by the control system of the contrast agent-administering facility. If the administration of contrast agent that has taken place up to now is, for example, part of a contrast agent-administering procedure that is still ongoing, it is possible, if the filling level was still too low up to now, for the filling pressure to be automatically increased for the further course of the contrast agent-administering procedure in order to achieve better filling levels. At the same time, it is possible to react quickly in the case of an excessive filling pressure, for example, filling levels above 100%, and to reduce the filling pressure by actuating the contrast agent-administering facility. In this connection, it is particularly expedient if the filling level information may be provided in real time, and this may be easily achieved, in particular, when artificial intelligence and the simple calculation approaches described here for the absorption values and the filling level are used.

Apart from the method, the disclosure also relates to an evaluation facility for evaluating a two-dimensional X-ray image showing a contrast agent in a hollow organ structure, in particular a vascular tree, in a recording region of a patient, recorded with an X-ray facility using X-ray radiation of an X-ray spectrum. The evaluation facility includes a segmenting unit for segmenting the hollow organ structure in the X-ray image. The evaluation facility further includes a measuring unit for determining center lines and edge boundaries of the segmented hollow organ structure and ascertaining a respective diameter of each hollow organ of the segmented hollow organ structure along its center line. The evaluation facility further includes a first ascertaining unit for ascertaining an image absorption value describing the increase in absorption due to the contrast agent in the hollow organ compared to surroundings of the hollow organ in the X-ray image, along the center line of each hollow organ, in particular for each position along the center line for which a diameter was ascertained. The evaluation facility further includes a second ascertaining unit for ascertaining a theoretical computing absorption value expected when the hollow organ is completely filled with the contrast agent, using at least the diameter and contrast agent information describing a composition and/or absorption properties of the contrast agent for each image absorption value. The evaluation facility further includes a determining unit for determining a filling level along the center line of each hollow organ of the hollow organ structure by comparing the image absorption value with the computing absorption value. The evaluation facility further includes an interface for outputting filling level information including the filling levels.

In other words, the evaluation facility is configured to carry out the method disclosed herein. The evaluation facility may include at least one processor and at least one storage device, it being possible for the functional units to be provided at least partially by the processor, in particular by hardware and/or software. Further functional units, in order to implement further acts of the method, may likewise be provided accordingly. For example, a correction unit may also be present to allow corrections of further imaging effects to be included. All statements in respect of the method may be analogously transferred to the evaluation facility with which the advantages already mentioned may also be obtained.

An X-ray facility has a control facility with an evaluation facility, as described herein. All previous statements continue to apply to the X-ray facility as well. The X-ray facility includes at least one recording arrangement with an X-ray tube assembly and an X-ray detector, it being possible for the X-ray image to be recorded by the recording arrangement. In this regard, the control facility may also have a recording unit to control the recording mode of the X-ray facility. For example, the X-ray image may be recorded as part of a series of X-ray images while the contrast agent flows through the hollow organ structure, it being possible to provide a particular frame rate. This may be a fluoroscopic or radiographic examination.

The X-ray facility may be, in particular, an X-ray facility having a C-arm, frequently employed in angiography laboratories, to which the X-ray tube assembly and the X-ray detector are fixed opposite each other. The C-arm may be brought into different positions to record X-ray images in different projection geometries or recording geometries. The X-ray facility may also have a biplane X-ray facility having two C-arms, which have one recording arrangement respectively.

In certain examples, the X-ray facility includes an automatic contrast agent-administering facility with a control unit actuating it. The control unit includes an interface for receiving the filling level information and being embodied for use of the filling level information in actuating the contrast agent-administering facility, in particular, for adjusting an injection pressure during a contrast agent-administering procedure to which the filling level information relates. The control unit may be part of the control facility. As already described above, the filling pressure may thus be adjusted by appropriate actuation of the contrast agent-administering facility by the control unit, even during a contrast agent-administering procedure, on the basis of the filling level information which may be obtained quickly, e.g., in real time. For example, such a contrast agent-administering procedure may last several seconds.

The procedure may be used for a wide variety of contrast agents. Contrast agents including iodine and/or carbon dioxide may be considered.

A computer program may be directly loaded into a storage device of an evaluation facility and has program means configured to carry out the acts of the method disclosed herein when the computer program is executed on the evaluation facility. The computer program may be stored on an electronically readable data carrier, which therefore includes control information stored thereon, which information includes at least one computer program and is configured in such a way that it embodies this, when the data carrier is used in an evaluation facility, to carry out acts of the method when the computer program is executed on the evaluation facility.

BRIEF DESCRIPTION OF THE DRAWINGS

Further advantages and details of the present disclosure may be found in the exemplary embodiments described below and with reference to the drawings, in which.

DETAILED DESCRIPTION

Figure 1:
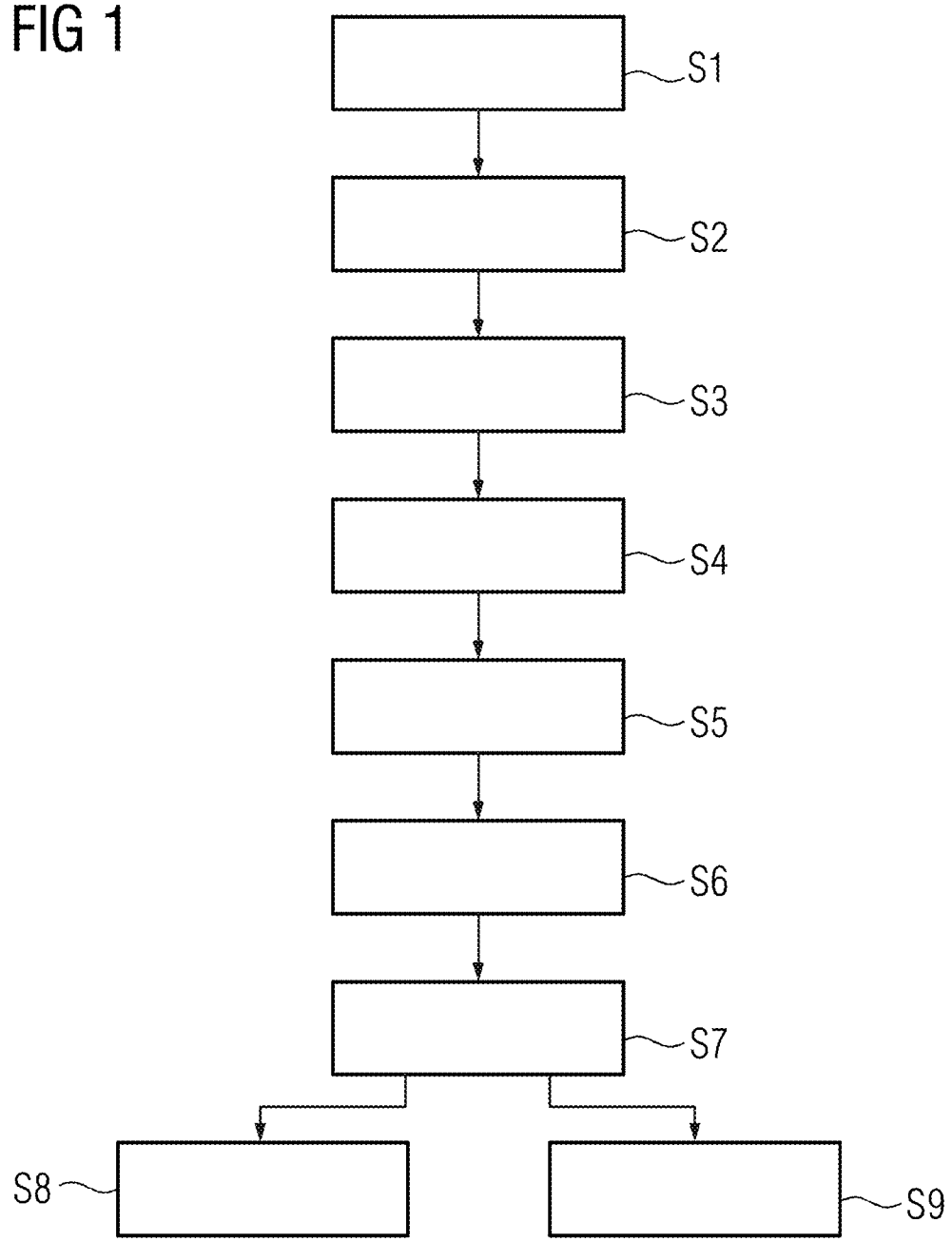
FIG. 1 depicts a flowchart of an exemplary embodiment of the method.

FIG. 1 shows a flowchart of an exemplary embodiment of the method, with a blood vessel system, in particular a vascular tree, being used in the present case as an example of a hollow organ structure, wherein the hollow organs are blood vessels. A contrast agent has already been administered in advance manually or using an automatic contrast agent-administering facility to a patient.

Therefore, in act S1, an X-ray image of a recording region of the patient including the hollow organ structure may be recorded with an X-ray facility in which the hollow organ structure is more visible owing to the contrast agent. The X-ray image may be part of a time series of X-ray images, which may serve for fluoroscopic monitoring of a procedure, for radiographic examination, and/or with different recording geometries, also for reconstruction of a three-dimensional image dataset. X-ray images are recorded with an X-ray spectrum, which may be set using the tube voltage. A multi-energy application, in particular dual-energy imaging, is also possible in which, for example, alternately or in the case of a biplane X-ray facility also simultaneously, high- and low-energy X-ray spectra are used.

Filling level information is now to be ascertained for the X-ray image recorded in act S1 in that a comparison is made with the information theoretically expected with a filling level of 100%. For this purpose, the absorption taking place due to the contrast agent is firstly to be determined in a spatially resolved manner from the image values of the X-ray image.

In act S2, the hollow organ structure is segmented in the X-ray image. Segmenting algorithms basically known in the prior art may be used in this case, in particular also those which derive, moreover, certain measurement information from the segmenting result, and this occurs in act S3 of the method. Namely, the center lines of the hollow organs, (e.g., blood vessels), their edge boundaries, and their diameters are to be derived, with round blood vessels, those with a circular cross-section may be assumed within the framework of the present disclosure. Artificial intelligence, for example, in the form of at least one trained function, in particular a CNN, may be at least partially used for segmenting and/or ascertaining center lines, edge boundaries and diameters along the center lines.

When segmenting and/or ascertaining center lines, edge boundaries, and diameters, further information, (e.g., segmenting results or other information from further X-ray images forming part of the time series and/or from prior recordings and/or optionally also from reconstruction results using the X-ray image), may also be used in addition to the X-ray image. An anatomical atlas may also be used.

Figure 2:
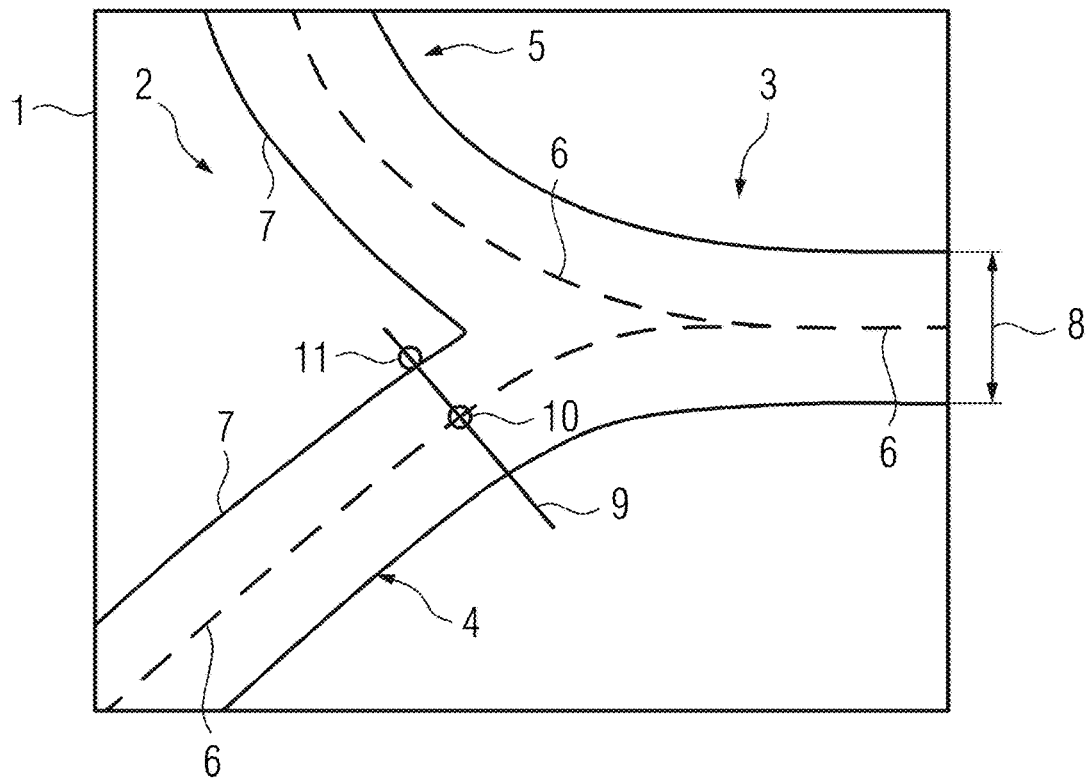
FIG. 2 schematically depicts an X-ray image having annotations based on the method.

By way of explanation, FIG. 2 shows purely schematically a detail from an X-ray image 1 in which a hollow organ structure 2, kept simple for illustrative purposes, having, in the present case, the hollow organs 3, 4, 5 is shown. The center lines 6 and the edge boundaries 7 are determined here during the segmenting. The corresponding diameters 8 may then be derived herefrom perpendicular to the center lines 6.

Returning to FIG. 1, the absorption for different positions along the center lines 6 in the X-ray image 1 is then measured in act S4 in that an image absorption value is determined. All points along the center lines 6, for which a diameter 8 is known, are considered for determining the respective image absorption value. As indicated in FIG. 2, at a location for the hollow organ 4, a straight line 9 perpendicular to the center line 6 is determined. In addition, at least one image point forms a center line region 10 containing the center line 6. The number of image points (e.g., pixels) from which the center line region 10 is formed may be selected on the basis of the spatial resolution of the X-ray image 1. In the present case, one image point is used by way of example. In addition, progress is made outwardly along the straight line 9 until the edge boundary 7 has been crossed in order to define a reference region 11 outside of the hollow organ structure 2, the hollow organs 3, 4, 5 therefore, in particular adjoining the corresponding hollow organ 4 as closely as possible, which reference region likewise includes at least one image point. For example, at least the first or the second image point along the straight line 9 may be selected, which is no longer located inside the segmented hollow organ structure 2, the edge boundary 7, therefore.

In the case of center line regions 10 and reference regions 11 formed by a single image point, the image values of the center line regions 10 directly result in a respective hollow organ image value; the image values of the reference regions 11 in a respective image value of the surroundings. With regions 10, 11 including a plurality of image points, a statistical averaging may take place.

The image absorption value is now ascertained in that the difference in the image value of the surroundings and the hollow organ image value is divided by the image value of the surroundings. This describes the share of the "basic intensity" (image value of the surroundings) extremely accurately, which also ceases to exist owing to the passage of contrast agent.

A computing absorption value is then also ascertained in act S5 for each image absorption value. The Beer Lambert law is used for this in the present case in which law the absorption along a section of the length of the diameter 8 (on the basis of the assumption of the circular hollow organ 4, 3, 5) completely filled with contrast agent is determined by way of calculation. The contrast agent composition or the contrast agent properties determine the extinction values to be used in this case. Because these may also be dependent on the energies of the X-ray radiation, it is possible to also use spectrum information, which describes the X-ray spectrum. A distinction may be made between high- and low-energy spectra here although a more accurate break-down or even the use of a functional correlation is also conceivable. If a beam hardening is to be taken into consideration, and if the relative position of the hollow organ 3, 4, 5 in the patient currently being examined is known, the spectrum information may also still be modified accordingly, owing to the radiation hardening expected due to the radiographing of the patient, in order to take this imaging effect into consideration.

The computing absorption value is likewise determined as a ratio of intensities. It therefore indicates, likewise as a percentage, to what extent the contrast agent would provide attenuation if it were present throughout the entire hollow organ 3, 4, 5. The computing absorption value may be directly compared with the image absorption value therefore, with a further important imaging effect, namely the scattered radiation, also being taken into consideration in act S5, however, before the comparison taking place in act S6 for ascertaining the filling level.

While a scattered radiation correction may be applied to the X-ray image 1, and thus not modify ascertainment of the computing absorption value, in certain examples, a share of the provisional value corresponding to a percentage correction value and resulting from the Beer Lambert law may be deducted from it to definitively determine the computing absorption value. The correction value corresponds to the share of the scattered beams in the overall signal for the image value of the surroundings.

Once this correction has been made the filling level may be ascertained in act S6 as the image absorption value divided by the computing absorption value, because the quotient of the absorption describes how much contrast agent is actually present.

This shall be explained using a few specific examples. In a first example, the X-ray image was recorded with a tube voltage of 89 kV using a 0.3 mm copper filter. The patient has a thickness to be radiographed of 300 mm and the SID is 1,110 mm (SID=source image distance). The vessel diameter at an examined position of a blood vessel as a hollow organ 3, 4, 5 is 4.45 mm. With an iodine-containing contrast agent and 100% filling, an expected absorption, as a provisional computing absorption value therefore, of 60.5% then results, with the correction for the radiation by the correction value of 26% still having to be taken into consideration, however, so 44.5% is obtained as the computing absorption value to be used. Forty two percent is measured in the image as the image absorption value, however. This results in a filling level of 94%.

In a second exemplary embodiment, an X-ray image of the recording region of a 420 ml thick patient with an SID of 1,200 mm was recorded with a tube voltage of 123 kV using a 0.2 mm copper filter. The vessel diameter was 3 mm here. With 100% filling with the contrast agent an absorption of 32% then firstly results by way of calculation from the Beer Lambert law. If, on the basis of the correction value of 45%, which describes the scattered radiation, approximately 14% is deducted as the correction value, a computing absorption value of 18% results. If 14% was measured as the image absorption value, the result is a filing level of approximately 77%.

The filling level, like the diameter in act S6, is calculated along all center lines 6. The filling level information that thus results is output at the interface in act S7. Basically, various options are conceivable in this connection. It is thus possible, for example, to represent the filling level information at least partially on a display facility in act S8, in particular a display facility of the X-ray facility.

Figure 3:
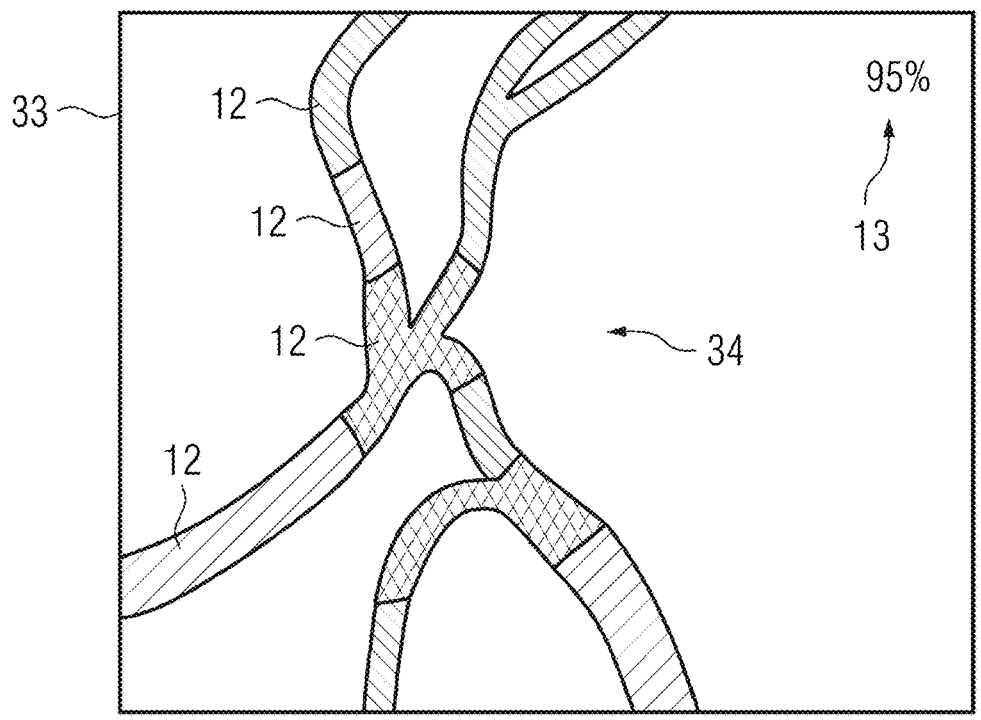
FIG. 3 depicts an example of a display on a display facility.

FIG. 3 shows an exemplary display image 33 in which the filling level information of a hollow organ structure map 34 is shown superimposed and color-coded. The different hatchings in the region 12 represent different colors for different efficiency rate ranges. Warning colors, in particular red tones, are expediently used for color coding in the case of filling levels exceeding a threshold value, for example, 100%.

In addition, the display image 10 also shows the maximum occurring filling level, here 95%, as the number 13.

The filling level information may also be stored in a storage facility for subsequent further evaluation. However, it is also possible, when automated contrast agent-administering facilities are used, to forward, in accordance with act S9 (cf. FIG. 1), the filling level information to a control unit of the contrast agent-administering facility, for example a contrast agent injector, where it is taken into consideration for control. In particular, it is also conceivable in the case of at least substantially real-time determination of the filling level information, to draw conclusions, relating to contrast agent that has already been administered, during a contrast agent-administering procedure from X-ray images 1 for a necessary adjustment of the filling pressure and to thus optimize the use of contrast agent over the contrast agent-administering procedure.

Figure 4:
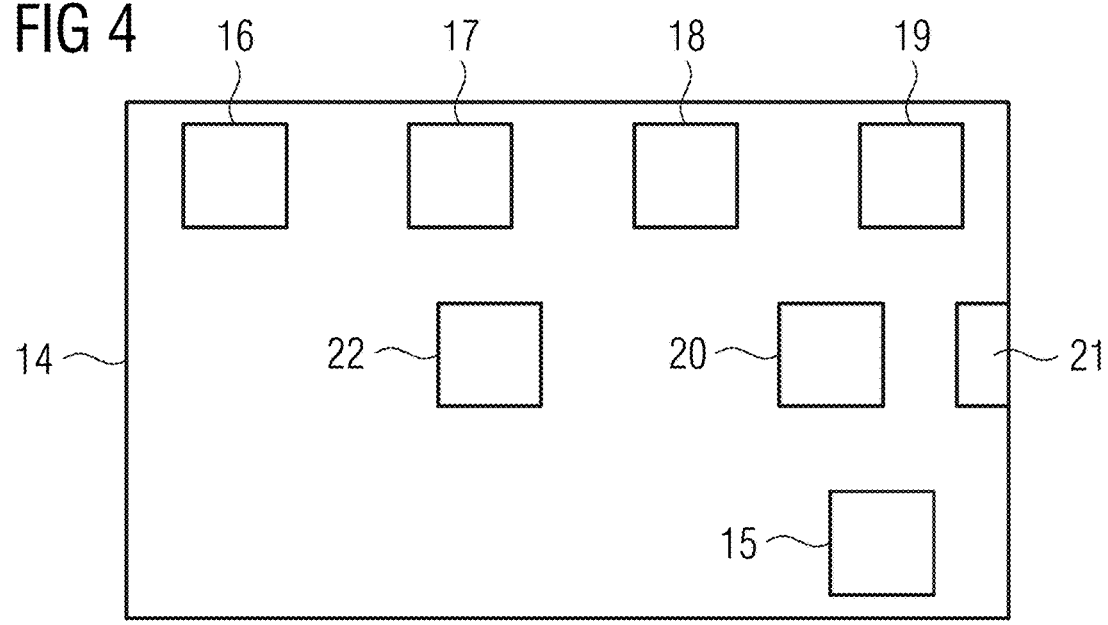
FIG. 4 depicts an example of a functional structure of an evaluation facility.

FIG. 4 shows the functional structure of an evaluation facility 14. Apart from a storage device 15, the evaluation facility includes a segmenting unit 16 for carrying out act S2. For determining center lines, edge boundaries, and diameters, a measuring unit 17 is provided, which implements act S3 accordingly. A first ascertaining unit 18 for ascertaining the image absorption value is embodied for carrying out act S4, while a second ascertaining unit 19 is configured for carrying out act S5, for ascertaining the computing absorption value. The filling level along the center lines 6 is determined in a determining unit 20 in accordance with act S6 and thus the filling level information, which may then be provided in accordance with act S7 via an interface 21. Further functional units may also be provided, for example, a correction unit 22 for implementing the beam hardening correction (modification of the spectrum information) and the scattered radiation correction (determining and applying the signal component).

Figure 5:
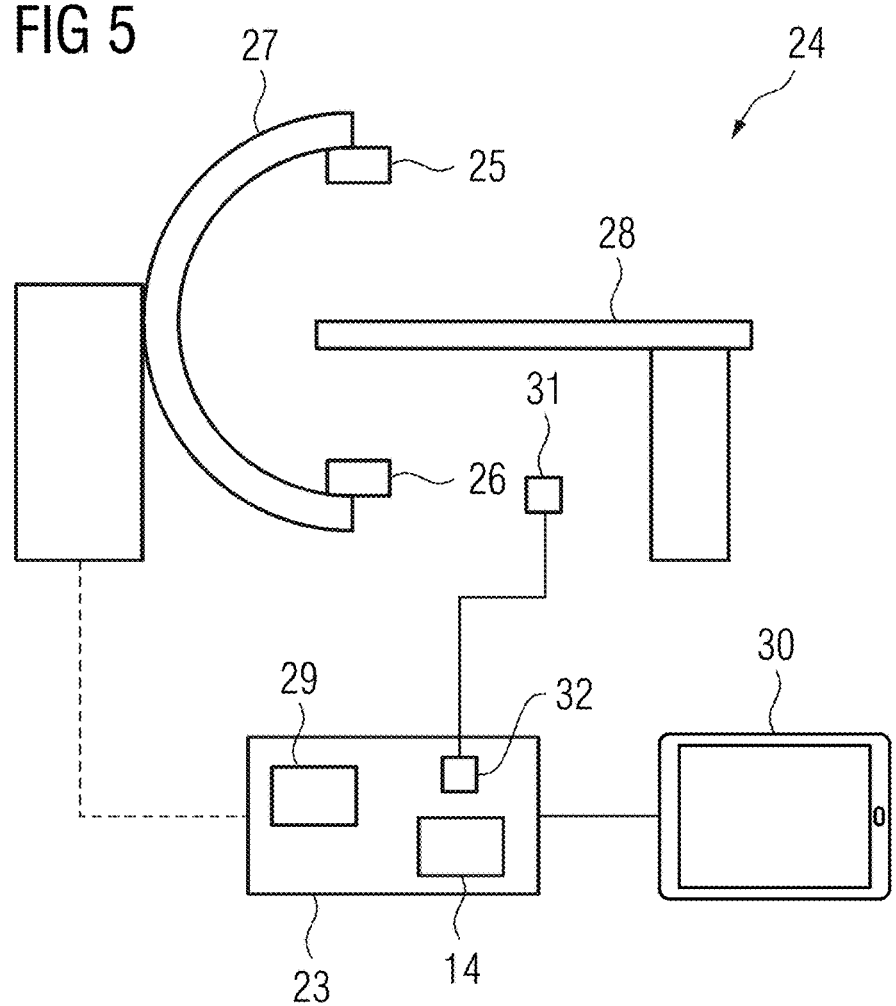
FIG. 5 depicts a schematic diagram of an example of an X-ray facility.

The evaluation facility may be part of the control facility 23 of an X-ray facility 24 schematically represented in FIG. 5. In the present case, the X-ray facility 24 includes, as a recording arrangement, an X-ray tube assembly 25, and an X-ray detector 26, which are arranged opposite each other on a C-arm 27. This may be brought into various positions in respect of a patient arranged on a patient couch 28. For controlling the recording mode of the X-ray facility 24, in particular also for recording the X-ray image in act S1, the control facility also has a recording unit 29. A display facility 30 is assigned to the control facility 23, for example, for representing the filling level information in accordance with act S8.

In the present case, the X-ray facility 24 also includes an automatic contrast agent-administering facility 31, here a contrast agent injector, which is controlled by a control unit 32 that is similarly situated in the control facility 23. This is configured for carrying out act S9. The filling level information may therefore be taken into consideration in the control of the contrast agent-administering facility 31, in particular during a continuous contrast agent-administering procedure, in particular with regard to the optimization of the filling level.

Although the disclosure has been illustrated and described in detail by the exemplary embodiments, it is not limited by the disclosed examples and a person skilled in the art may derive other variations herefrom without departing from the scope of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A computer-implemented method for evaluating a two-dimensional X-ray image showing a contrast agent in a hollow organ structure in a recording region of a patient, recorded with an X-ray facility using X-ray radiation of an X-ray spectrum, wherein the hollow organ structure is a vascular tree, the method comprising:
   segmenting the hollow organ structure in the X-ray image;
   determining center lines and edge boundaries of the segmented hollow organ structure and ascertaining a diameter of each hollow organ of the segmented hollow organ structure along a center line of the respective hollow organ;
   ascertaining an image absorption value, describing an increase in absorption due to the contrast agent in the respective hollow organ compared to surroundings of the respective hollow organ in the X-ray image, along the center line of each hollow organ for each position along the center line for which a diameter was ascertained;
   ascertaining, for each image absorption value, a theoretical computing absorption value expected when the respective hollow organ is completely filled with the contrast agent, by using at least the diameter and contrast agent information describing a composition of the contrast agent, absorption properties of the contrast agent, or a combination thereof;
   determining a filling level along the center line of each hollow organ of the hollow organ structure by comparing the image absorption value with the theoretical computing absorption value; and
   outputting filling level information comprising the filling level of each hollow organ.

2. The method of claim 1, wherein the ascertaining of the diameter of the respective hollow organ in the segmented hollow organ structure and/or the computing of the absorption value takes place under an assumption of a circular cross-section of the respective hollow organ.

3. The method of claim 1, wherein, in the ascertaining of each image absorption value, a ratio of an amount of a difference of a hollow organ image value in a center line region comprising at least one image point around the center line and an image value of surroundings in a reference region comprising at least one additional image point and located outside of the segmented hollow organ structure from the image value of the surroundings in the reference region is ascertained.

4. The method of claim 3, wherein the center line region and/or the reference region comprises a plurality of image points, and
   wherein the respective image value to be used in the ratio is ascertained by statistical weighted averaging of the image values of the X-ray image over the plurality of image points.

5. The method of claim 3, wherein the reference region directly adjoins the hollow organ and/or lies in a cutting plane running through the center line region.

6. The method of claim 1, wherein, in the ascertaining of the theoretical computing absorption value, Beer Lambert law is used for X-ray radiation of the X-ray spectrum, which passes through a section of the contrast agent corresponding to the diameter.

7. The method of claim 1, wherein, in the ascertaining of the theoretical computing absorption value and/or the image absorption value, at least one further imaging effect is taken into consideration, and
   wherein the at least one further imaging effect comprises a beam hardening effect, a scattered radiation effect, or a combination thereof.

8. The method of claim 7, wherein, for scattered radiation correction, a percentage correction value is ascertained that describes a ratio of scattered radiation to an overall signal for a reference region, and a share, corresponding to a correction value of the theoretical computing absorption value ascertained using Beer Lambert law, is subtracted from it.

9. The method of claim 1, further comprising:
   displaying at least a portion of the filling level information on a display of the X-ray facility.

10. The method of claim 9, wherein the displayed filling level information is displayed superimposed and spatially resolved, in particular color-coded, on the X-ray image and/or a hollow organ structure map ascertained from the segmented hollow organ structure.

11. An evaluation facility configured to evaluate a two-dimensional X-ray image showing a contrast agent in a hollow organ structure in a recording region of a patient recorded with an X-ray facility using X-ray radiation of an X-ray spectrum, wherein the hollow organ structure is a vascular tree, the evaluation facility comprising:
- a segmenting unit configured to segment the hollow organ structure in the X-ray image;
- a measuring unit configured to determine center lines and edge boundaries of the segmented hollow organ structure and ascertain a respective diameter of each hollow organ of the segmented hollow organ structure along a center line of the respective hollow organ;
- a first ascertaining unit configured to ascertain an image absorption value, describing an increase in absorption due to the contrast agent in the respective hollow organ compared to surroundings of the respective hollow organ in the X-ray image, along the center line of each hollow organ for each position along the center line for which a diameter was ascertained;
- a second ascertaining unit configured to ascertain a theoretical computing absorption value expected when the respective hollow organ is completely filled with the contrast agent, using at least the diameter and contrast agent information describing a composition of the contrast agent, absorption properties of the contrast agent, or a combination thereof;
- a determining unit configured to determine a filling level along the center line of each hollow organ of the hollow organ structure by comparing the image absorption value with the theoretical computing absorption value; and
- an interface configured to output filling level information comprising the filling level of each hollow organ.

12. An X-ray facility comprising:
- a control facility having an evaluation facility configured to evaluate a two-dimensional X-ray image showing a contrast agent in a hollow organ structure in a recording region of a patient recorded with an X-ray facility using X-ray radiation of an X-ray spectrum, wherein the hollow organ structure is a vascular tree, the evaluation facility comprising:
  - a segmenting unit configured to segment the hollow organ structure in an X-ray image;
  - a measuring unit configured to determine center lines and edge boundaries of the segmented hollow organ structure and ascertain a respective diameter of each hollow organ of the segmented hollow organ structure along a center line of the respective hollow organ;
  - a first ascertaining unit configured to ascertain an image absorption value, describing an increase in absorption due to the contrast agent in the respective hollow organ compared to surroundings of the respective hollow organ in the X-ray image, along the center line of each hollow organ for each position along the center line for which a diameter was ascertained;
  - a second ascertaining unit configured to ascertain a theoretical computing absorption value expected when the respective hollow organ is completely filled with the contrast agent, using at least the diameter and contrast agent information describing a composition of the contrast agent, absorption properties of the contrast agent, or a combination thereof;
  - a determining unit configured to determine a filling level along the center line of each hollow organ of the hollow organ structure by comparing the image absorption value with the theoretical computing absorption value; and
  - an interface configured to output filling level information comprising the filling level of each hollow organ.

13. The X-ray facility of claim 12, further comprising:
an automatic contrast agent-administering facility,
wherein the control facility is further configured to:
- actuate the contrast agent-administering facility; and
- receive the filling level information and use the filling level information when actuating the contrast agent-administering facility for adjusting a filling pressure during a contrast agent-administering procedure to which the filling level information relates.

* * * * *